United States Patent [19]
Schneider-Nieskens

[11] Patent Number: 6,066,220
[45] Date of Patent: May 23, 2000

[54] PROCESS FOR PRODUCING A PROSTHESIS FOR THE FEMALE BREAST

[75] Inventor: Reinhold Schneider-Nieskens, Adendorf, Germany

[73] Assignee: Thämert Orthopädische Hilfsmittel GmbH & Co. KG, Burgwedel, Germany

[21] Appl. No.: 09/070,990

[22] Filed: May 1, 1998

[51] Int. Cl.⁷ ..................................................... A61F 2/52
[52] U.S. Cl. .................. 156/145; 156/245; 623/7
[58] Field of Search .................... 156/145, 245, 156/292; 623/7

[56] References Cited

U.S. PATENT DOCUMENTS

| | | | |
|---|---|---|---|
| 3,067,431 | 12/1962 | Kausch | 623/7 |
| 3,852,833 | 12/1974 | Koneke | 623/7 |
| 4,195,639 | 4/1980 | Lee | 623/7 |
| 4,249,975 | 2/1981 | Rechenberg | 623/7 |
| 4,401,492 | 8/1983 | Pfrommer | 156/145 |
| 4,701,230 | 10/1987 | Loi | 156/145 |
| 4,950,291 | 8/1990 | Mulligan | 623/7 |
| 5,370,688 | 12/1994 | Schulz et al. | 623/7 |
| 5,603,791 | 2/1997 | Weber-Unger | 156/145 |
| 5,902,335 | 5/1999 | Snyder | 623/7 |

FOREIGN PATENT DOCUMENTS

| | | |
|---|---|---|
| 0178483B1 | 4/1989 | European Pat. Off. . |
| 0396230B1 | 11/1994 | European Pat. Off. . |
| 3416240A1 | 11/1985 | Germany . |
| 0205349A2 | 12/1986 | Germany . |
| 3742352A1 | 6/1989 | Germany . |
| 3942608A1 | 7/1991 | Germany . |
| 9201918 | 6/1992 | Germany . |
| 9315935 | 2/1995 | Germany . |
| 4421516C1 | 7/1995 | Germany . |
| 4413076A1 | 10/1995 | Germany . |
| 29519283 U1 | 4/1996 | Germany . |
| 29607969 U1 | 6/1996 | Germany . |
| 29516281 U | 2/1997 | Germany . |

*Primary Examiner*—Daniel Stemmer
*Attorney, Agent, or Firm*—Collard & Roe, P.C.

[57] ABSTRACT

A process for producing a breast prosthesis having substantially cup-shaped prosthesis body. The first step in the process includes placing at least two plastic foils on top of each other. The next step involves shaping these foils into a pouch-like container. Once the pouch like container is formed, the edges of each plastic foil are joined to form at least two chambers. Next, at least one chamber is filled with material wherein the first material in the chamber is partially vulcanized. The second chamber is then filled with a second material. Finally, the prosthesis is cured in a molding die.

13 Claims, 1 Drawing Sheet

PROCESS FOR PRODUCING A PROSTHESIS FOR THE FEMALE BREAST

BACKGROUND OF THE INVENTION

1. Field of the Invention

The invention relates to a process for producing a breast prosthesis with a substantially bowl-shaped prosthesis body. the body is formed by placing at least two plastic foils one on top of the other. A pouch-like container having chambers is formed by connecting the edges of the foils. Each chamber is filed with a soft elastic material, which is subjected to vulcanization after it is placed in a molding die.

2. The Prior Art

Female breast prostheses are used to compensate or cover visually noticeable consequences of surgical interventions. The cup-like bodies of breast prostheses normally consist of soft elastic material, mainly silicone rubber. Such a material has a relatively high density, which has adverse effects on the wearing comfort of a large prosthesis (because of their weight). To reduce the weight of a breast prosthesis, lightweight fillers can be substituted into the silicone rubber compounds and then the mixture is shaped to the body of the prosthesis.

Unfortunately, the lightweight fillers change the properties of the silicone, resulting in disadvantageous effects to the breast prosthesis. For example, the hysteresis is considerably increased by the inner friction of the vulcanized compound. Furthermore, a silicone admixed with lightweight fillers has poor adherence to surrounding protective skin or foils. The foils have the function of keeping the body of the prosthesis in shape. However, such foils cannot perform this function if the lightweight fillers in the silicone rubber compound act as a release agent deteriorating the filter's adhesion to foils.

Furthermore, it is difficult to provide a consistent color to compound mixed with fillers because the fillers act like white pigments due to total reflection. The compound used for breast prosthesis, cannot be dyed in glazing colors, which would be useful, but instead has to be dyed in covering colors, which leads the unfavorable appearance of the breast prosthesis.

SUMMARY OF THE INVENTION

Therefore, the invention provides a process for producing a lightweight prosthesis consisting of a cup-shaped prosthesis body that has lightweight fillers having better adhesion and color properties, and thus can be manufactured very simply.

This invention solves this problem in that at least one of the outer chambers is filled with a first material and the material present in at least one of the outer chambers is at least partially vulcanized outside of the molding die. In addition, at least one inner chamber is subsequently filled with a second material. The prosthesis body is thereafter vulcanized in a molding die.

The inner core consisting of the second material constitutes most of the weight of the prosthesis body. The cover layer is made of a first material, which according to the invention is formed by the outer chambers. This cover layer provides the shape of the breast prosthesis which approximates the form of natural tissue. In addition, the cover layer also assumes a supporting and protective function for the inner core, which approximates the natural human skin and also feels like natural human skin. Therefore, the hysteresis of the breast prosthesis and the mechanical strength are improved. Moreover, there are less of problems with coloring the prosthesis because the first material for the outer chambers is glazed and thus can be readily dyed with a natural color.

The second material, which represents the inner core formed by the inner chamber, is a silicone compound mixed with 10% to 25%, but preferably 18% lightweight fillers. The inner core has a density of 0.3 g/cm$^3$, to 0.8 g/cm$^3$ but preferably 0.64 g/cm$^3$. The inner core therefore has a substantially lower density than the average density of a natural female breast, which is about 0.9 to 1 g/cm$^3$. The breast prosthesis is consequently light weight and offers a pleasant feeling when worn, because it produces less pressure on the straps of a brassiere receiving the prosthesis. These features are particularly beneficial to women requiring a relatively large breast prosthesis.

The lightweight fillers preferred are micro glass spheres with a particle size of 20 to 100 $\mu$, particularly about 75 $\mu$. Organic fillers can also be used as well. The inner core may consist of a polyurethane foam or silicone foam material. This design reduces the weight of the prosthesis. However, in the breast prosthesis according to this invention, the inner core is provided with at least one cover layer, so that it is possible to reduce the weight 20%–40% without adversely affecting the usual appearance of a breast prosthesis.

The first material, used to produce the cover layers by means of the outer chambers, is a conventional two-component silicone rubber compound that is cross-linked. Such a compound can be processed and used in the usual way.

The inner core, which is formed by an inner chamber, can be provided with a cover layer both on its convex and concavely arched surface. Since the elasticity of the silicone rubber compounds can be readily adjusted, it is possible to adjust the cover layer on the convex surface to be slightly harder so as to better imitate a more natural support similar to human skin.

On the other hand, the cover layer can be adjusted to create a particularly soft prosthesis to enhance the wearing comfort. The concave outer layer may contain about 20% to 70%, but preferably 50% less material than the first material. This number is based on the amount of the first material used for the convex cover layer, which is again advantageous for reducing the weight. Cover layers of different thickness can be formed in this way, so that the outer convex cover layer becomes the thicker layer. Thus, the surface of the breast prosthesis that has high external mechanical stresses is provided with the highest mechanical strength by the cover layer. For example, the concave cover layer may have a thickness of from 1 to 5 mm, and the convex cover layer may have a thickness of from 2 to 8 mm.

Another way to reduce the weight of the prosthesis is to provide each cover layer with a maximum thickness within the zone of its apex of curvature and thus with an approximately sickle-shaped cross section. In this design, there is increased dimensional stability (shape retention) without having to add any additional filler. The breast prosthesis has the highest mechanical strength in this region because in this region the supporting cover layer is thicker than in other regions. Thus, the prosthesis is most stable in the zone of its apex, namely where the inner core has its greatest thickness, and thus a material accumulation, which has to be supported and protected.

With the breast prosthesis of the invention, at least one plastic foil is present on the boundaries between the inner core and the cover layers, as well as on the free surfaces of the cover layers. Each foil consists of a thermoplastic polyurethane polymer that has a thickness of about 40 $\mu$ to 80 $\mu$.

The plastic foils are fused with each other on the edge of the cup-like body of the prosthesis. Thus, the inner core and cover layers are enclosed in each case between the plastic foils.

The breast prosthesis can be easily manufactured. Several foils, preferably four, are placed on top of each other and fused to each other along their edges, so that foil bags are correspondingly formed between the layers. Fusing can be interrupted in certain areas to allow apertures to be formed. The still empty foils, disposed one on top of each other are now uniformly held or chucked in one plane on a chucking board or plate so that the foils are elastically prestressed by an elongation of 1% to 4%. The two chambers, can subsequently be filled with standard breast prosthesis silicone gel as the first material. In this case, the outer chamber facing the chucking board receives about 20% to 70%, but preferably 50% less filling than the outer chamber facing away from the chucking board. The center inner chamber formed between the two foils each disposed on the inner side, remains initially unfilled. The natural initial tension assures that the silicone gel of the first material is uniformly and evenly distributed in the outer chambers between the foils and ends along their edges. The distribution of the silicone can be further helped by setting the chucking board in a tilted position. Furthermore, defined trough-shaped recesses or depressions may be provided in the chucking board, which may aid in the distribution of the second material as well. The chucking board with the first material filled in the outer chambers is now placed in an oven and fully vulcanized or cured at a temperature that does not fuse the foils.

Following the steps of curing the first material, the entire foil package is chucked in a mold or similar die. The center inner chamber, between the two inner foils of the foil package, can now be filled with a mixture selected as the second material within the closed mold or closed die. The mixture for the second material consists of a two-component silicone gel, to which lightweight fillers, preferably micro glass spheres have been added. It is also possible to use organic fillers as light weight filling material, such as plastic hollow spheres or balls.

The entire prosthesis can now be cured in a circulating air oven within 1 to 2 hours, preferably within 75 minutes between 140° to 170° C., but preferably 150° C. During this time, the foils embedded in the silicone between the first material and the second material are jointly shaped in this process.

Following cooling, the breast prosthesis as defined by the invention is removed from the die, and the projecting foil edge is pinched off. It is essential to the invention to have the silicone layers of the outer chambers to be partly or fully cured before the inner core is produced. The invention provides silicone parts, or components with elastic cover layers without requiring any considerable cost expenditure in terms of tools.

BRIEF DESCRIPTION OF THE DRAWINGS

Other objects and features of the present invention become apparent from the following detailed description considered in connection with the accompanying drawing which discloses an embodiment of the present invention. It should be understood, however, that the drawing is designed for the purpose of illustration only, not as a definition of the limits of the invention.

In the drawing, wherein similar reference characters denote similar elements throughout the two views.

DETAILED DESCRIPTION OF PREFERRED EMBODIMENTS

Figure 1:
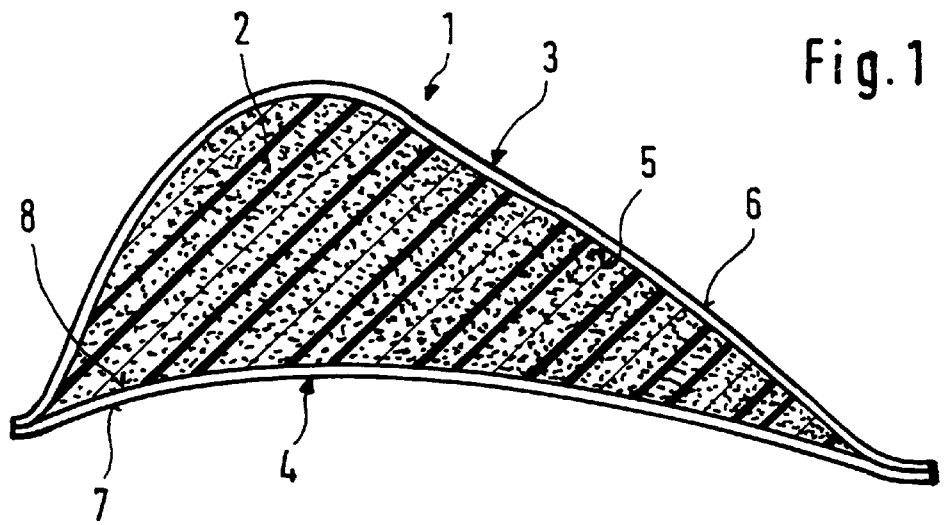
FIG. 1 is a side cross-sectional view of the breast prosthesis of the invention.
Figure 2:
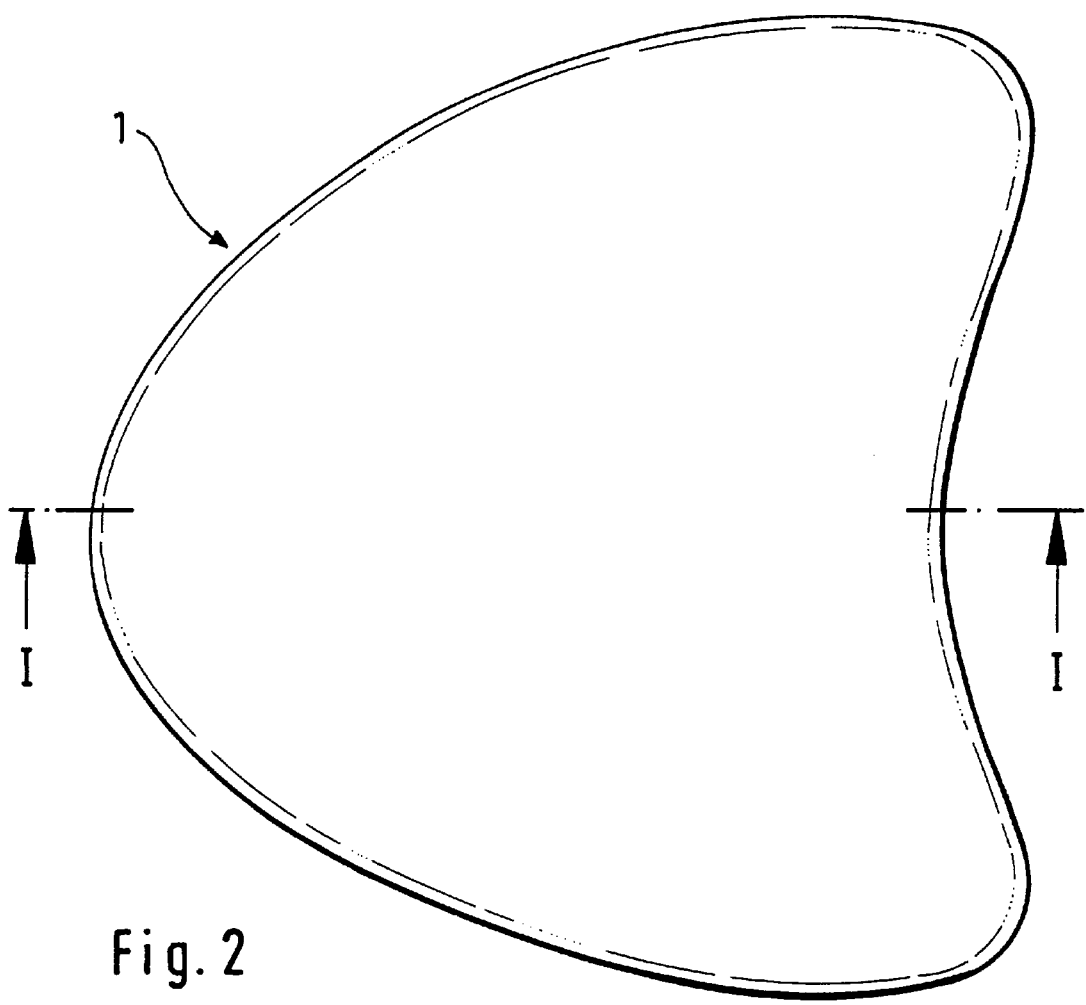
FIG. 2 is a top view of the breast prosthesis of FIG. 1.

Referring to, FIG. 1, there is shown a side cross-sectional view of one embodiment of the breast prosthesis. The latter consists of a prosthesis body 1 having an approximately cup- or dish-like shape. The prosthesis body is formed by an inner core 2, which is housed within a cover layer 3 on its convex surface, and a cover layer 4 on its concavely arched surface.

The inner core consists of a second material, namely a silicone, to which a 10% to 20%, and preferably 16% lightweight fillers are added in order to reduce the weight of the inner core and thus the entire prosthesis. A first material, namely a commonly used standard silicone gel is used for cover layers 3 and 4.

Each cover layer, consisting of standard silicone gel is embedded between two foils 5, 6, 7 and 8 made of thermoplastic polyurethane elastomer with a thickness of about 40 $\mu$ to 80 $\mu$. Foils 5 and 6 form the area of the convex surface of prosthesis body 1 while foils 7 and 8 form the opposite concave surface on body 1.

While one embodiment of the present invention has been shown and described, it is to be understood that many changes and modifications may be made thereunto without departing from the spirit and scope of the invention as defined in the appended claims.

What it is claimed:

1. A process for producing a breast prosthesis having a substantially cup-shaped body comprising the steps of:
   a) placing a plurality of plastic foils on top of each other;
   b) shaping said foils into a cup-shaped container;
   c) joining the edges of each plastic foil to form at least one inner chamber and at least one outer chamber;
   d) filling said at least one outer chamber with a first material;
   e) providing a mold;
   f) vulcanizing said first material within said at least one outer chamber outside of said mold;
   g) filling said at least one inner chamber with a second material; and
   h) curing the prosthesis comprising said at least one inner chamber with said second material and said at least one outer chamber with said first material within said mold to form said prosthesis.

2. The process according to claim 1, wherein step a) comprises placing four foils one on top of each other, step c) includes fusing said foils to each other along their edge wherein three chambers are formed, and said process further comprising the steps of clamping said prosthesis on one plane on a plate, and filling two outer chambers with said first material.

3. The process according to claim 2, wherein the outer chamber facing the plate is filled with 20% to 70% less amount of said first material than the outer chamber facing away from the plate.

4. The process according to claim 2, wherein the outer chamber facing the plate is filled with about 50% less amount of said first material than the outer chamber facing away from the plate.

5. The process according to claim 2, further comprising the step of controlling the distribution of said first material by setting the plate up in a tilted position.

6. The process according to claim 2, wherein step f further comprises the step of placing the plate in an oven and vulcanizing the first material at a temperature below the fusing temperature of the foil.

7. The process according to claim 2, further comprising the steps of removing said prosthesis from said plate, clamping said prosthesis in a said mold, closing the mold, filling said at least one inner chamber with said second material, and placing the mold in an oven so that the entire prosthesis is vulcanized.

8. The process according to claim 1, wherein the second material used for the inner core is a silicone compound admixed with light-weight filler material having a density between 0.3 g/cm$^3$ to 0.8 g/cm$^3$.

9. The process according to claim 8, wherein micro glass spheres are used as lightweight filler material.

10. The process according to claim 8, wherein organic fillers are used as lightweight filler material.

11. The process according to claim 1, wherein a polyurethane foam is used as the second material.

12. The process according to claim 1, wherein a silicone foam is used as the second material.

13. The process according to claim 1, wherein the first material is a two-component silicone rubber compound that is cross-linked by addition.

* * * * *

UNITED STATES PATENT AND TRADEMARK OFFICE
CERTIFICATE OF CORRECTION

PATENT NO. : 6,066,220
DATED : May 23, 2000
INVENTOR(S) : SCHNEIDER-NIESKENS

It is certified that error appears in the above-identified patent and that said Letters Patent is hereby corrected as shown below:

On the title page, column 1, after Item [22], please insert

[30]    Foreign Application Priority Data

| May 3, 1997 | [DE] | Germany | 197 18 851.6 |
| Dec. 5, 1997 | [DE] | Germany | 197 54 144.5 |

Signed and Sealed this

First Day of May, 2001

Attest:

NICHOLAS P. GODICI

Attesting Officer    Acting Director of the United States Patent and Trademark Office